(12) United States Patent
Zarins et al.

(10) Patent No.: US 7,083,576 B2
(45) Date of Patent: Aug. 1, 2006

(54) BIOPSY MARKER DELIVERY SYSTEM

(76) Inventors: Sascha Zarins, 1684 Cassair Dr., Los Altos, CA (US) 95130; Steven Kim, 2029 Crist Dr., Los Altos, CA (US) 94026

( * ) Notice: Subject to any disclaimer, the term of this patent is extended or adjusted under 35 U.S.C. 154(b) by 45 days.

(21) Appl. No.: 10/639,050

(22) Filed: Aug. 11, 2003

(65) Prior Publication Data

US 2004/0049126 A1 Mar. 11, 2004

Related U.S. Application Data

(63) Continuation of application No. 09/954,792, filed on Sep. 10, 2001, now Pat. No. 6,605,047.

(51) Int. Cl.
*A61B 10/00* (2006.01)

(52) U.S. Cl. ............... 600/562; 600/431; 606/116; 604/116

(58) Field of Classification Search ............ 600/12, 600/414, 420, 424, 426, 431, 562, 564, 566, 600/567; 604/19, 57, 59, 60, 62, 63, 164.01, 604/164.11; 606/116, 117, 142, 143, 151, 606/167; 40/300; 128/897–899
See application file for complete search history.

(56) References Cited

U.S. PATENT DOCUMENTS

| | | |
|---|---|---|
| 4,230,123 A | 10/1980 | Hawkins, Jr. |
| 4,699,154 A | 10/1987 | Lindgren |
| 4,890,626 A | 1/1990 | Wang |
| 4,944,308 A | 7/1990 | Akerfeldt |
| 4,953,558 A | 9/1990 | Akerfeldt |
| 5,092,870 A | 3/1992 | Mittermeier |
| 5,108,421 A | 4/1992 | Fowler |
| 5,197,484 A | 3/1993 | Kornberg et al. |
| 5,353,804 A | 10/1994 | Kornberg et al. |
| 5,388,588 A | 2/1995 | Nabai et al. |
| 5,394,886 A | 3/1995 | Nabai et al. |
| 5,467,780 A | 11/1995 | Nabai et al. |
| 5,526,822 A | 6/1996 | Burbank et al. |
| 5,560,373 A | 10/1996 | De Santis |
| 5,571,181 A | 11/1996 | Li |
| 5,643,291 A | 7/1997 | Pier et al. |
| 5,645,566 A | 7/1997 | Brenneman et al. |
| 5,649,547 A | 7/1997 | Ritchart et al. |
| 5,810,806 A | 9/1998 | Ritchart et al. |
| 5,817,033 A | 10/1998 | De Santis et al. |
| 5,902,310 A | 5/1999 | Foerster et al. |
| 5,906,599 A | 5/1999 | Kaldany |
| 5,913,857 A | 6/1999 | Ritchart et al. |
| 5,951,494 A | 9/1999 | Wang et al. |
| 5,980,469 A | 11/1999 | Burbank et al. |
| 6,006,750 A | 12/1999 | Field |
| 6,019,733 A | 2/2000 | Farascioni |
| 6,056,700 A | 5/2000 | Burney et al. |
| 6,142,955 A | 11/2000 | Farascioni |
| 6,220,248 B1 | 4/2001 | Voegele et al. |
| 6,228,055 B1 | 5/2001 | Foerster et al. |
| 6,234,177 B1 | 5/2001 | Barsch |
| 6,261,243 B1 | 7/2001 | Burney et al. |
| 6,261,302 B1 | 7/2001 | Voegele et al. |
| 6,347,241 B1 | 2/2002 | Burbank et al. |
| 6,350,244 B1 | 2/2002 | Fisher |
| 6,379,671 B1 | 4/2002 | Colpitts |
| 6,605,047 B1 * | 8/2003 | Zarins et al. ............ 600/562 |

FOREIGN PATENT DOCUMENTS

| | | |
|---|---|---|
| EP | 0 769 281 A2 | 4/1997 |
| WO | WO 96/08208 A1 | 3/1996 |

* cited by examiner

*Primary Examiner*—Charles Marmor

(57) ABSTRACT

An apparatus for delivering subcutaneous cavity marking devices. More particularly, the delivery devices may be used with biopsy systems permitting efficient placement of a biopsy marker within a cavity. The device may include an intermediate member which assists in deployment of the marking device. The devices may also include a deployment lock to prevent premature deployment of a biopsy marker. The invention may further include the capability to match an orientation of a biopsy probe which has been rotated upon procurement of a biopsy sample.

10 Claims, 8 Drawing Sheets

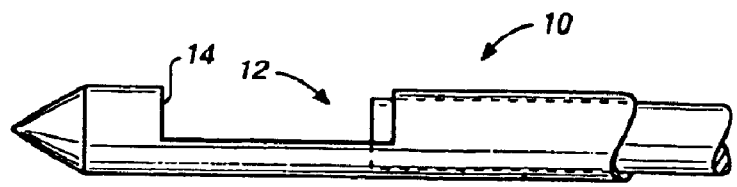
FIG._1A
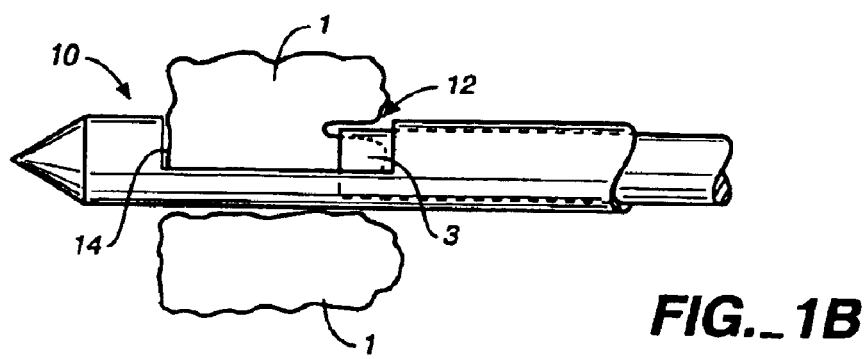
FIG._1B
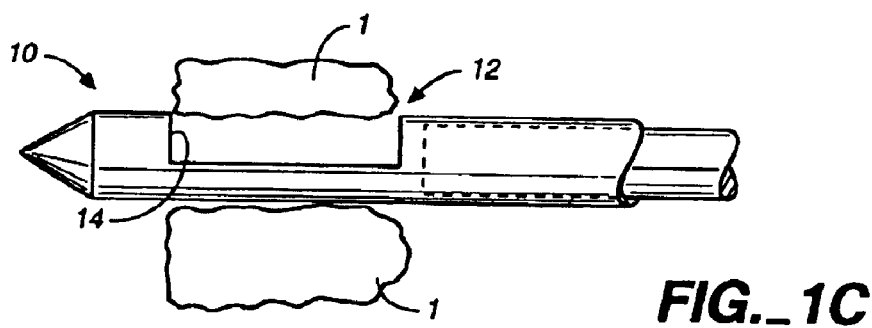
FIG._1C
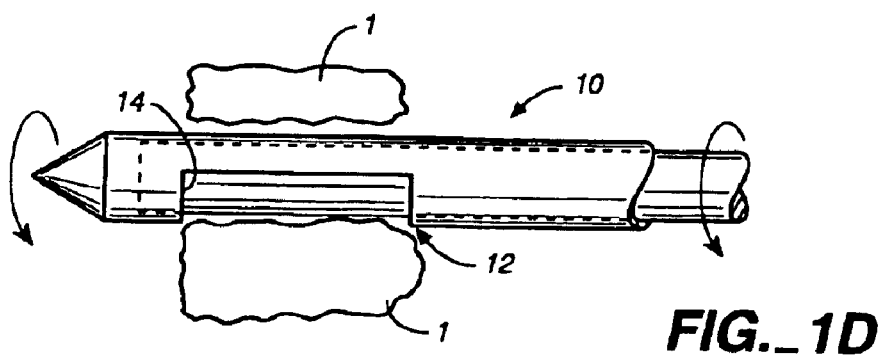
FIG._1D
Prior Art

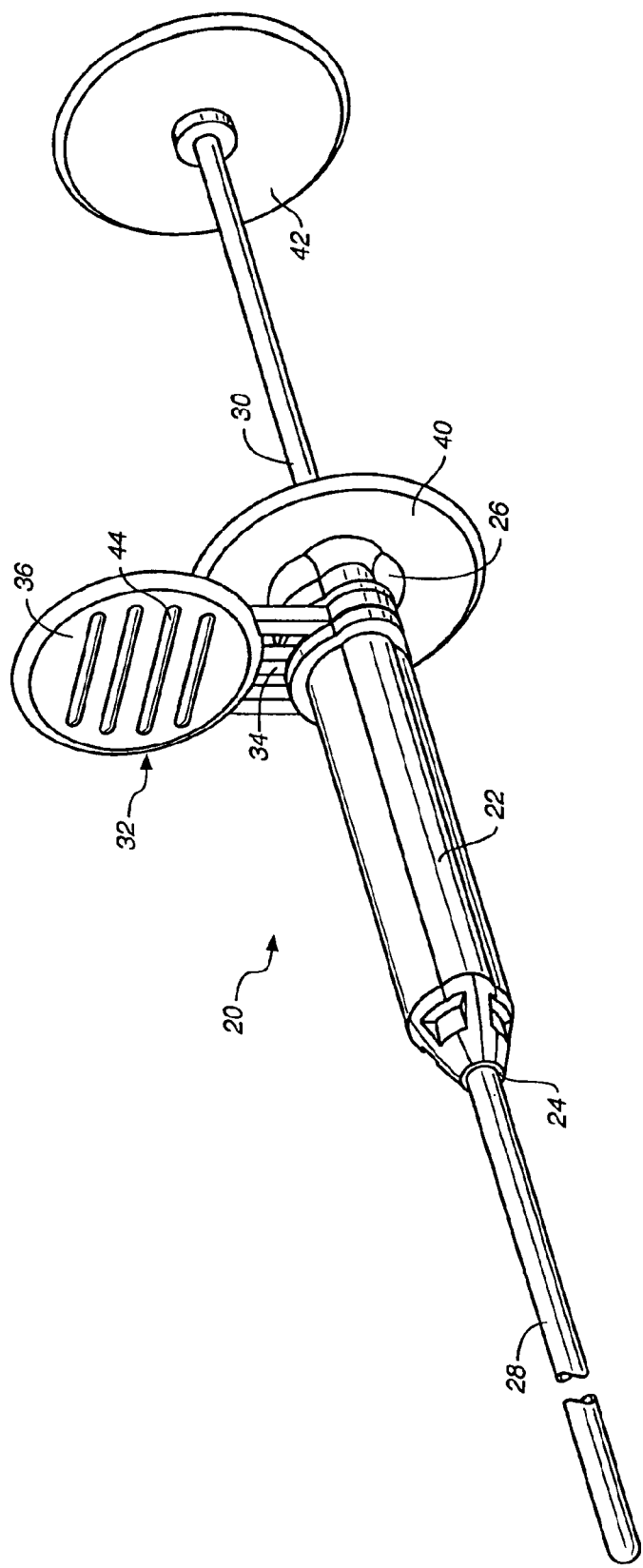
FIG._2

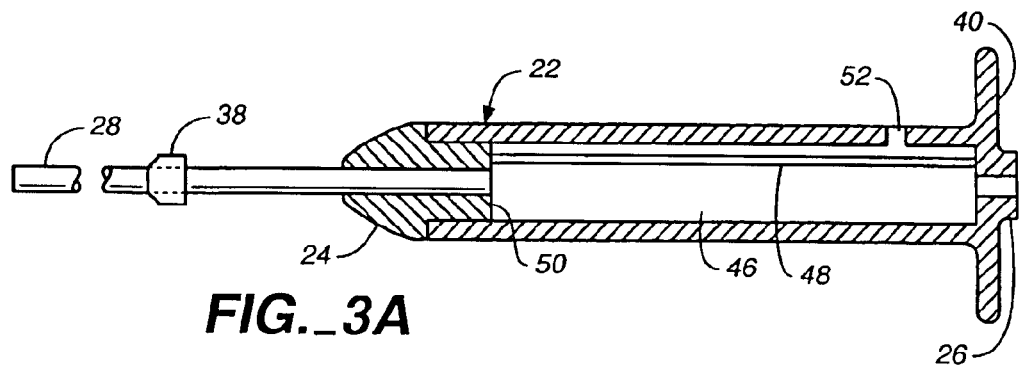
FIG._3A
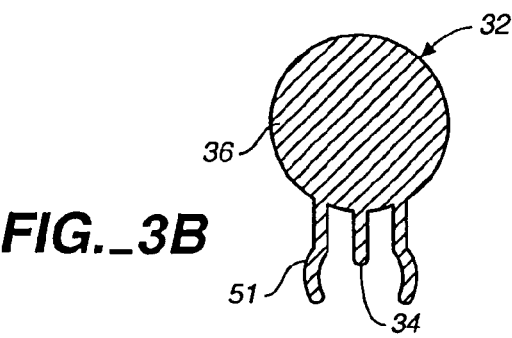
FIG._3B
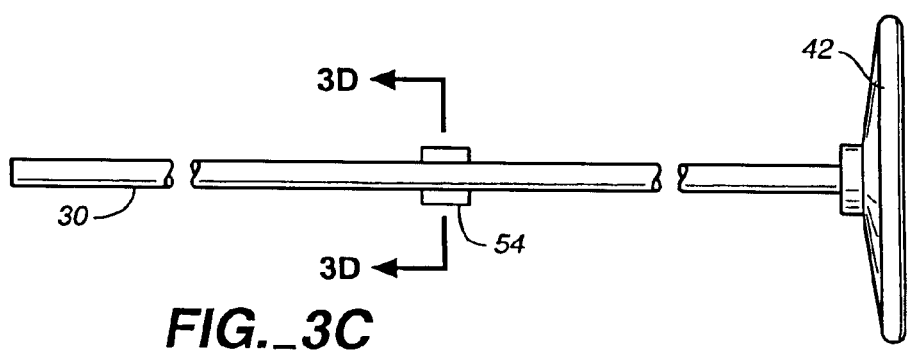
FIG._3C
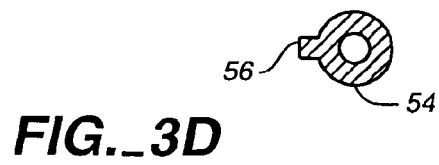
FIG._3D

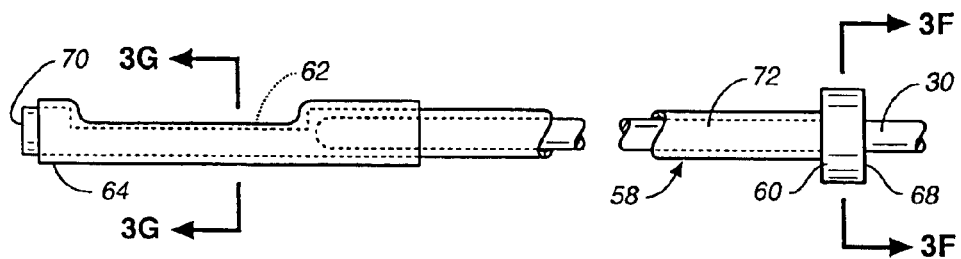
FIG._3E
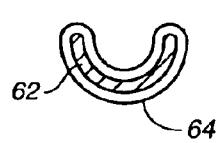
FIG._3G
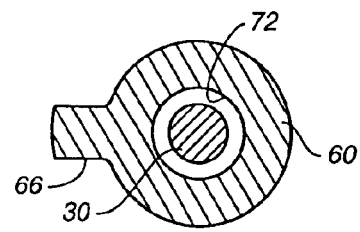
FIG._3F
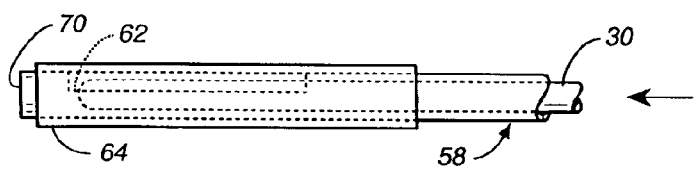
FIG._3H

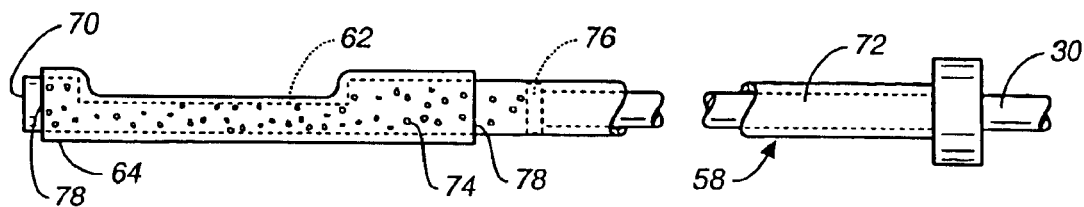
FIG._3I
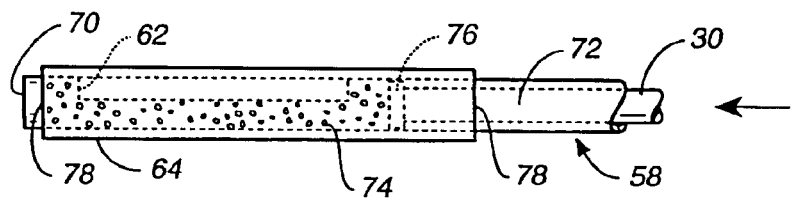
FIG._3J
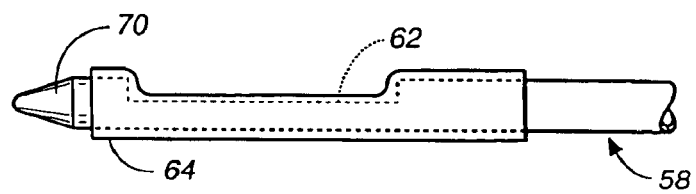
FIG._3K

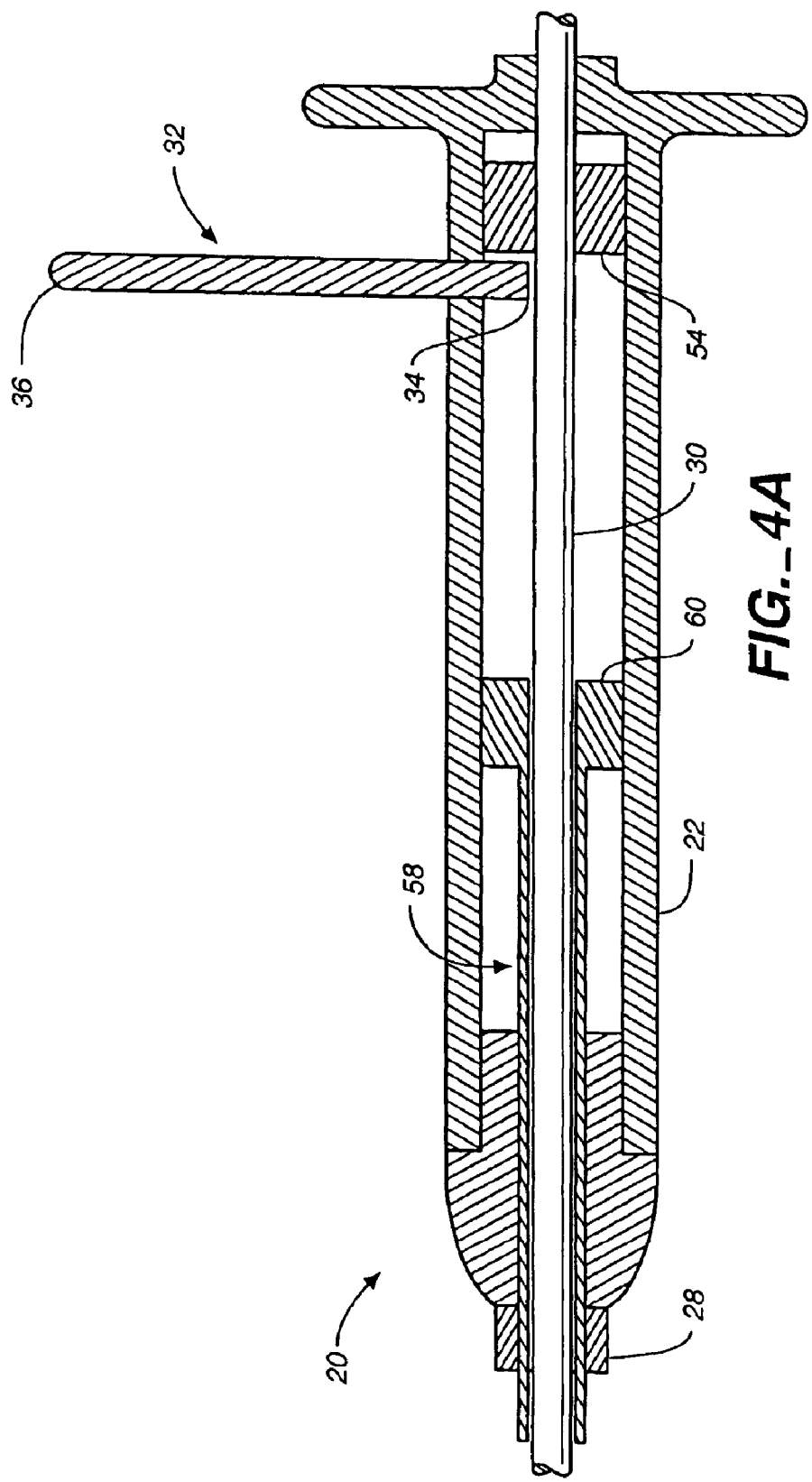
FIG._4A

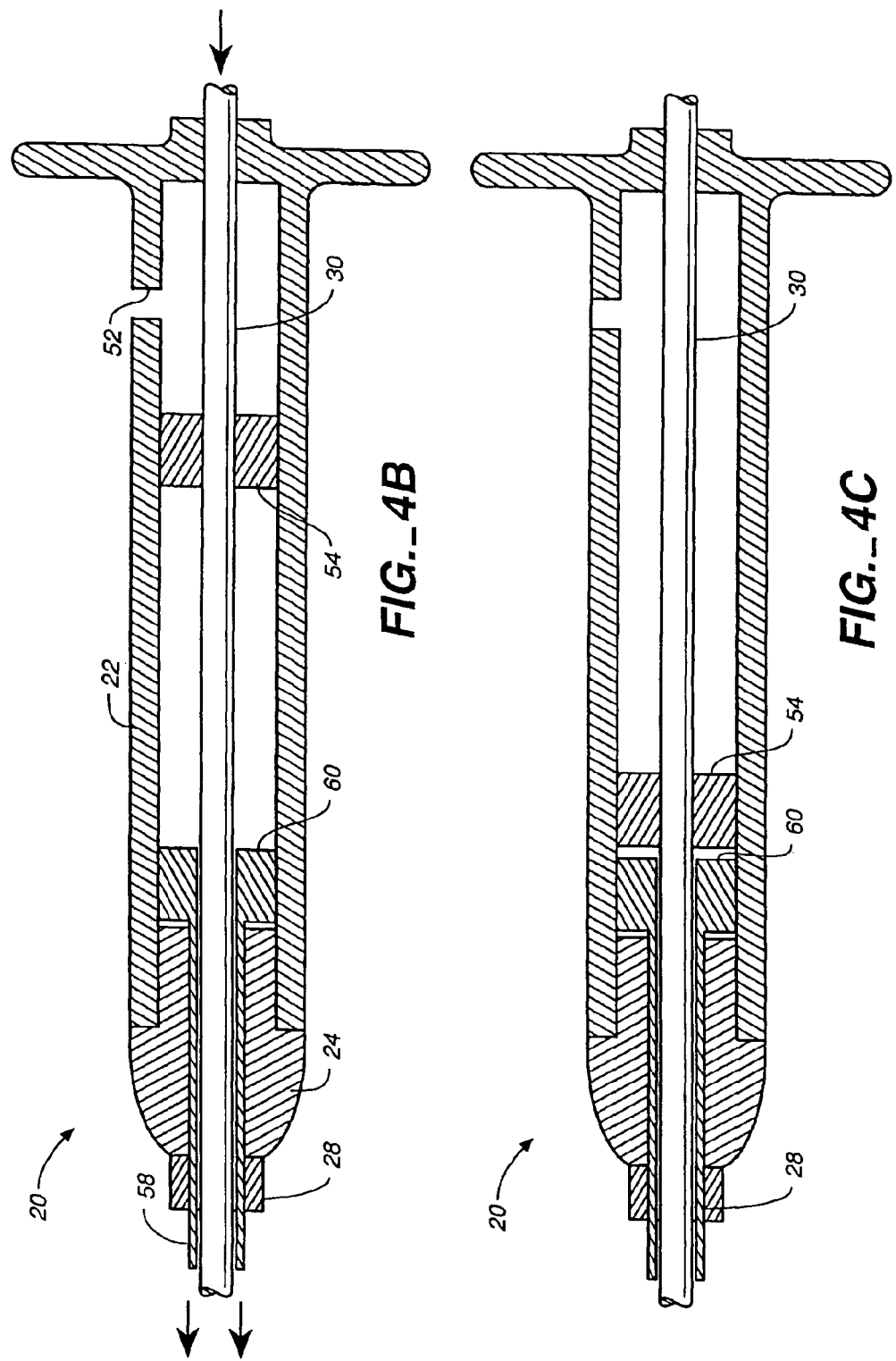

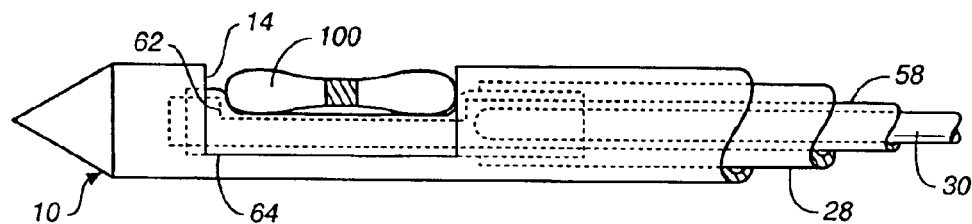
FIG._5A
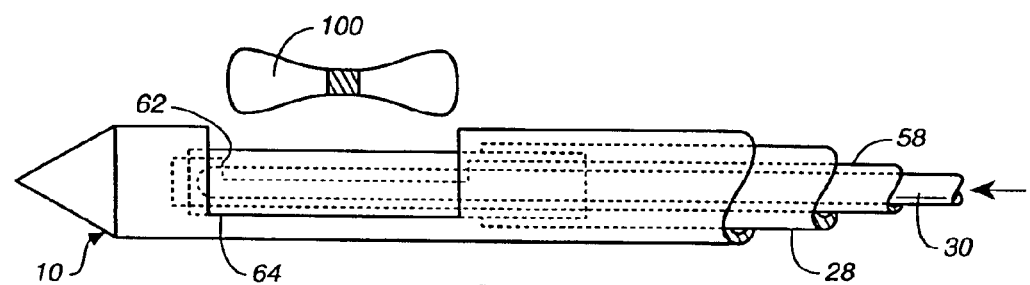
FIG._5B
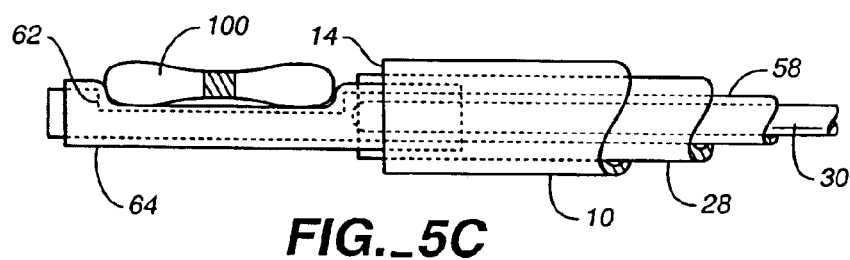
FIG._5C
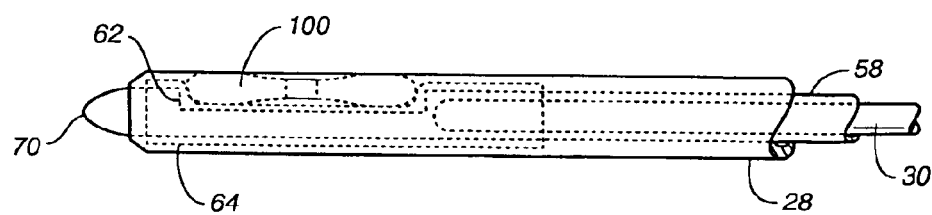
FIG._5D

BIOPSY MARKER DELIVERY SYSTEM

This application is a continuation of U.S. application Ser. No. 09/954,792, filed Sep. 10, 2001, now U.S. Pat. No. 6,605,047, the contents of which is hereby incorporated by reference into the present disclosure.

FIELD OF THE INVENTION

This invention is directed to delivery devices for delivering subcutaneous cavity marking devices. More particularly, the delivery device may be used with biopsy systems permitting efficient placement of a biopsy marker within a cavity. The device may include an intermediate member which assists in deployment of the marking device. The device may also include a deployment lock to prevent premature deployment of a biopsy marker. The invention may further include the capability to match an orientation of a biopsy probe that has been rotated upon procurement of a biopsy sample.

BACKGROUND OF THE INVENTION

Over 1.1 million breast biopsies are performed each year in the United States alone. Of these, about 80% of the lesions excised during biopsy are found to be benign while about 20% of these lesions are malignant.

In the field of breast cancer, stereotactically guided and percutaneous biopsy procedures have increased in frequency as well as in accuracy as modern imaging techniques allow the physician to locate lesions with ever-increasing precision. However, for any given biopsy procedure, a subsequent examination of the biopsy site is very often desirable. There is an important need to determine the location, most notably the center, as well as the orientation and periphery of the subcutaneous cavity from which the lesion is removed.

In those cases where the lesion is found to be benign, for example, a follow-up examination of the biopsy site is often performed to ensure the absence of any suspect tissue and the proper healing of the cavity from which the tissue was removed. This is also the case where the lesion is found to be malignant and the physician is confident that all suspect tissue was removed and the tissue in the region of the perimeter of the cavity is "clean".

In some cases, however, the physician may be concerned that the initial biopsy failed to remove a sufficient amount of the lesion. Such a lesion is colloquially referred to as a "dirty lesion" or "having a dirty margin" and requires follow-up observation of any suspect tissue growth in the surrounding marginal area of the initial biopsy site. Thus, a re-excision of the original biopsy site must often be performed. In such a case, the perimeter of the cavity must be identified since the cavity may contain cancerous cells. Moreover, the site of the re-excised procedure itself requires follow-up examination, providing further impetus for accurate identification of the location of the re-excised site. Therefore, a new marker may be placed after re-excision.

While biopsy markers are well known, examples of improved biopsy markers are described in U.S. Pat. No. 6,356,782, entitled "SUBCUTANEOUS CAVITY MARKING DEVICE AND METHOD" and U.S. Pat. No. 6,371,904, entitled "SUBCUTANEOUS CAVITY MARKING DEVICE AND METHOD" each of which is incorporated by reference herein. Placement of such biopsy markers may occur through either invasive surgical excision of the biopsy, or minimally invasive procedures such as fine needle aspiration or vacuum assisted biopsy.

In a fine needle aspiration biopsy, a small sample of cells is drawn by a thin needle from the lump or area of suspect tissue. If the suspect area or lump cannot be easily felt, non-invasive imaging may be used to help the doctor guide the needle into the right area. A core biopsy is similar to a fine needle aspiration biopsy, except that a larger needle is used. Under a local anaesthetic, the doctor makes a very small incision in the patient's skin and removes several narrow sections of tissue from the suspect area of tissue through the same incision. The core biopsy provides a breast tissue sample rather than just individual cells. Thus making it easier for the pathologist to identify any abnormalities.

Vacuum-assisted biopsy is performed through the skin and may rely upon ultrasound or stereotactic guidance to determine the location of a suspect area of tissue. Two commonly used vacuum-assisted breast biopsy systems are Mammotome® supplied by Johnson & Johnson Ethicon Endo-surgery or MIBB® supplied by Tyco International. Examples of such devices may be found in U.S. Pat. No. 5,526,822 entitled "Methods and Apparatus for Automated Biopsy and Collection of Soft Tissue," U.S. Pat. No. 5,649,547 entitled "Methods and Devices for Automated Biopsy and Collection," U.S. Pat. No. 6,142,955 entitled "Biopsy Apparatus and Method" and U.S. Pat. No. 6,019,733 entitled "Biopsy Apparatus and Method" the entirety of each of which is incorporated by reference herein. Such breast biopsy systems include a probe that is inserted through the skin and is usually adapted to provide a vacuum to assist in obtaining the biopsy sample.

FIGS. 1A–1D illustrate an exemplary biopsy probe 10. As illustrated, the distal ends of probes 10 of these biopsy systems are adapted to both penetrate tissue and to contain a cutting member 12 which facilitates the removal of the biopsy sample. The cutting member 12 will contain an aperture 14 (often referred to as a "probe window.") The aperture 14 may be located on a side of a probe 10.

Once inserted through the skin, the cutting member 12 of the probe 10 aligns with suspect tissue 1 via stereotactic, ultrasound, or other means. After proper positioning of the probe 10, a vacuum draws the breast tissue 1 through the probe aperture 14 into the probe 10. As illustrated in FIG. 1B, once the tissue 1 is in the probe 10, the cutting member 12 actuates to capture a tissue sample 3. The tissue sample 3 may then be retrieved through the probe 10 to a tissue collection area (e.g., a standard pathology tissue cassette). FIG. 1C illustrates the probe 10 after the tissue sample is cleared from the aperture 14. Note that the illustration depicts a portion of the cutting member 12 as being retracted, leaving aperture 14 open; the cutting member 12 may alternatively be placed in a closed position during retrieval of the tissue sample.

The biopsy system is often adapted such that the cutting member 12 and aperture 14 rotate (e.g., via manipulation of a thumbwheel on the probe or biopsy system) with respect to the biopsy system. After excision of a tissue sample from the area of suspect tissue, the radiologist or surgeon may rotate the probe 10 and the aperture 14 to a new position relative to the biopsy system. FIG. 1D illustrates the probe 10 and aperture 14 after being rotated but without being removed from the body. The rotation of the probe 10 and aperture 14 permits excision of multiple subsequent biopsy samples from a target area of suspect tissue with only a single insertion of the biopsy probe 10. It should be noted that FIG. 1D is provided merely to illustrate the rotation of the probe 10 within the body. As such, the placement of biopsy markers is not illustrated in the figure. Moreover, the cutting member 12 is depicted in a closed position. This may ease rotation of the probe 10 within the tissue.

The entire cycle may be repeated until sampling of all desired areas occurs (typically, 8 to 30 samples of breast tissue are taken up to 360 degrees around the suspect area). Accordingly, it is important that the operator of the biopsy system is able to identify the orientation of the probe aperture 14 relative to the biopsy system at any given time while the probe aperture 14 remains within the tissue. Often, demarcations on the thumbwheel permit the identification of the probe orientation.

The above described removal of tissue samples creates tissue cavities. Hence, for reasons that are apparent to those familiar with such biopsy procedures, placement of a biopsy marker through the probe is most desirable. For example, repeated removal of the probe and insertion of a biopsy marking device may cause unneeded additional discomfort to the patient undergoing the procedure; removal of the probe may introduce error in placement of the biopsy marker into the desired location; repeated removal and insertion of each of the devices may prolong the duration of the procedure or spread cancer cells; after the probe removes a tissue sample, it is in the optimal location to deposit a marker; etc.

Biopsies may be performed with other tissue sampling devices as described in U.S. Pat. Nos.: U.S. Pat. Nos. 4,699,154; 4,944,308, and 4,953,558 the entirety of each of which is incorporated by reference herein. Such devices obtain a biopsy sample through a hollow biopsy needle having an aperture located in a distal end of the biopsy needle. As with the biopsy devices previously described, once the tissue sampling devices removes tissue and creates a biopsy cavity, it may be desirable to place a marker in the area of the biopsy cavity.

In view of the above, there remains a need for an improved biopsy marker delivery system that may facilitate placement of a biopsy marker and also may be used with commercially available biopsy systems.

SUMMARY OF THE INVENTION

This invention relates to delivery systems for delivery of biopsy cavity marking devices. A basic variation of the invention includes a tissue marker delivery device comprising a tube having a lumen extending therethrough, a tissue marker removably seated in a distal end of the tube, a rod slidably located within the tube lumen and having a first end extending through a proximal end of tube and a second end in the tube lumen; and an intermediate member separating the rod from the biopsy marker, where advancement of the rod in a distal direction displaces the intermediate member to displace the tissue marker from said marker seat. In a variation of this invention, the intermediate member is discrete from both the rod and the tissue marker. The intermediate member may comprises a flexible covering as described herein.

Another variation of the invention includes a delivery device for use with a biopsy probe having an aperture, the delivery device comprising a body having proximal and distal ends and a passageway extending therethrough, an elongate sheath having a lumen extending therethrough, the sheath extending distally from the distal end of the body, the sheath lumen in fluid communication with the body passageway, an access tube having a proximal and a distal end and a lumen extending from at least a portion of the access tube through the proximal end, the access tube slidably located within the body passageway and the sheath lumen, a marker seat located towards the distal end of the access tube, a rod slidably located within the access tube lumen and having a first end extending through the proximal end of the body and a second end in communication with the marker seat, wherein advancement of the rod in a distal direction advances the marker seat distally until the marker seat is adjacent to the probe aperture such that a marker in the marker seat may be deployed from the aperture. For example, when using a biopsy probe having an aperture in a side wall of the probe, the marker seat may be advanced within the aperture and subsequently deploys a marker. When the inventive device is used with biopsy probes having an aperture in a distal end of the probe, the marker seat may be advanced just proximal to the aperture in preparation for subsequent deployment of the marker.

The rod may advance the marker seat through a number of configurations. For example, the rod may be sized to have an interference fit with a portion of the access tube lumen. Another example includes a device configured such that the rod engages a marker which is situated in the marker seat. In such a case, a sheath may restrain the marker in the marker seat. Thus, until the marker is no longer constrained by the sheath, the rod will advance the marker within the sheath. In another variation, the rod may be in communication with a fluid that is itself in communication with the marker seat. In such a case, the rod may apply a force on the fluid to advance the marker seat and/or displace a marker from the marker seat. In some variations, the fluid may serve to displace a flexible covering out of the marker seat. It is contemplated that the rod of the present invention may advance the marker seat through a combination of configurations either described herein or known to those familiar with similar delivery devices.

A variation of the invention also includes a delivery device as described above, wherein the body further comprises a keyway along the passageway, and the body has an orientation being defined relative to the keyway, the delivery device further comprising an access tube key located on the access tube and adapted to be slidably located within the body keyway, the access tube key adapted to maintain an orientation of the access tube with the body orientation.

Variations of the invention may also include a deployment lock having a first end and a second end, the first end moveably located in the body and the second end located outside of the body, the first end adapted to engage a portion of the rod to prevent at least distal movement of the rod, whereupon disengagement of the first end of the deployment lock from the portion of the rod permits distal movement of the rod. The deployment lock may be removable from the device or may be moveable within the device so as to permit disengagement of the lock from the rod while still being attached to the body of the device.

The invention also may include a rod stop fixedly located on the rod, wherein after the rod is advanced into the marker seat, the rod stop engages the access tube stop preventing further distal movement of the rod. The rod stop may also include a rod key that is adapted to maintain an orientation of the rod with the body orientation.

A variation of the device includes an access tube stop fixedly located on a portion of the access tube being located within the body, wherein advancement of the rod in a distal direction advances the marker seat distally until the access tube stop engages the distal end of the body preventing further distal movement of the access tube whereupon further distal advancement of the rod advances into the marker seat. In one variation of the invention, engagement of the access tube stop against the distal end of the body places the marker seat adjacent to the biopsy probe aperture.

In another variation of the invention a portion of the distal end of the access tube is removed to define the marker seat.

The invention may also include a covering located over at least the marker seat, where at least a portion of the covering is adapted to displace into and out of the marker seat. Movement of the rod into the marker seat displaces the covering out of the marker seat. In variations of the invention using such a covering, there is no direct contact between the actuator (e.g., rod, etc.) and a marker placed within the marker seat.

In another variation of the invention, the inventive device includes a delivery device key adapted to seat in the biopsy probe and maintain an orientation of the access tube with an orientation of the biopsy probe. The delivery device key may be located on the elongated sheath or on the body of the device. In some variations of the invention, seating the delivery device key in the biopsy probe will cause a distal end of the outer sheath to be placed immediately proximal to the biopsy probe aperture.

Variations of the invention also may include a biopsy marker that is seated in the marker seat.

Although the delivery device and method described herein for delivering a marking device to a subcutaneous cavity is suited for use with a biopsy probe, the invention is not necessarily limited as such. Variations of the inventive device may be used with any type of biopsy procedure.

The invention also contains a kit containing a biopsy marker delivery device as described herein and an introducer cannula. The introducer cannula may be used to facilitate insertion of the delivery device into the patient to assist in delivery of a biopsy marker. The kit may also include a biopsy probe. The biopsy probe may be a spring-loaded biopsy probe.

The invention also includes a method for marking a biopsy cavity. In one variation, the inventive method includes using a delivery device having a marker, a tube removably seating the marker, a rod within the tube, and an intermediate member separating the rod and the marker, the method comprising, advancing the marker and delivery device to the biopsy cavity, actuating the rod to displace the intermediate member on the delivery device; and depositing the marker in the cavity upon displacing the intermediate member.

BRIEF DESCRIPTION OF THE DRAWINGS

FIG. 1A illustrates biopsy probe for use with variations of the present invention.

FIG. 1B illustrates the biopsy probe of FIG. 1A in which tissue is drawn through an aperture of the probe for excision of a biopsy sample.

FIG. 1C illustrates the biopsy probe of FIG. 1A where the biopsy sample is cleared from the aperture.

FIG. 1D illustrates the biopsy probe of FIG. 1A rotated within the body.

FIG. 2 provides a perspective view of a variation of a delivery device of the present invention.

FIGS. 3A–3K illustrate various components that may be used in delivery devices of the present invention.

FIGS. 4A–4C provide cross sectional views of a portion of a delivery device of the present invention during actuation of the device.

FIGS. 5A–5D illustrate cross sectional views of a delivery device of the present invention deploying a marker.

DETAILED DESCRIPTION OF THE INVENTION

The following discussion of the variations of the invention and the reference to the attached drawings are for explanatory purposes and do not exhaustively represent the possible combinations and variations of the invention. Those skilled in the art will readily appreciate that many variations may be derived using the following description. The following examples are intended to convey certain principles of the invention. These examples are not intended to limit the scope of the claims to any particular example. It is understood that the claims are to be given their broadest reasonable interpretation in view of the description herein, any prior art, and the knowledge of those of ordinary skill in the field. Furthermore, it is understood that the invention is not limited to the markers described herein. Instead, the invention may be used with any type of biopsy marker or tissue marker.

FIG. 2 illustrates a perspective view of a variation of a biopsy marker delivery device 20 of the present invention. In this variation, the delivery device 20 includes a body 22 having an elongate sheath 28 extending from a distal end 24 of the body 22 and a rod 30 extending from a proximal end 26 of the body 22. This variation of the device 20 also includes a deployment lock 32 having a first end 34 moveably located in the body 22 of the device 20 and second end 36 located outside of the body 22. As discussed below, the first end 34 of the deployment lock 32 engages a portion (not shown) of the rod 30 preventing distal movement of the rod. Disengagement of the first end 34 of the deployment lock 32 from the rod 30 permits movement of the rod 30 within the device 20.

As will be apparent, the device 20 may incorporate features to permit ease in handling the device 20. For example, the proximal ends of the body 22 and the rod 30 each may have portions 40, 42 of increased surface area that assist in the ability to actuate the device. Also, the second end 36 of the deployment lock may have raised surface areas 44 that permit an operator to grip the deployment lock 32 when an operator disengages the first end 34 of the deployment lock 32 from the rod 30. Such features, which permit ease in handling the device, are well known to those skilled in the art and are not meant to limit the scope of the invention.

FIG. 3A illustrates a cross sectional view of a body 22 and elongate sheath 28 of a variation of the inventive device. In this variation, the body 22 has a proximal end 26, a distal end 24, and a passageway 46 extending through the body 22. The variation of the body 22 depicted in FIG. 3A also contains a keyway 48 extending through at least a portion of the body passageway 46. As described below, the keyway 48 permits alignment and/or maintaining orientation of components of the inventive device with an orientation of the body 22. The ability to identify an orientation of the device relative to, for example, a biopsy probe is desirable for proper deployment of a biopsy marker. The keyway 48 may be a male or female keyway which permits mating of a corresponding key such that a component having such a key will maintain orientation while moved through the device.

In the variation depicted in FIG. 3A, the distal end 24 of body 22 includes an end component 50 that reduces a diameter of the passageway 46 therethrough. It should be noted that the body 22 may be optionally designed without such an end component 50. For example, the body 22 could be designed as a unitary piece. In variations where the body 22 is constructed as a unitary piece, the body passageway 46 may optionally have an area of reduced diameter at the distal end 24. This area of reduced diameter made from a uniform reduction of the diameter of the passageway 46 or may have one or more protrusions which effectively reduce the diameter of the passageway 46. The body 22 may also include an opening 52 through which a deployment lock may be inserted through the body 22. As discussed above, the body 22 may also include a portion 40 of increased surface area that permits handling of the device. The body may be formed out of materials such as ABS, polycarbonate, acetal, or acrylic.

The inventive device also includes an elongate sheath 28 extending distally from a distal end 24 of the body 22. The elongate sheath 28 contains a lumen (not shown) that extends through the sheath 28. The sheath lumen is in fluid communication with the body passageway 46. By fluid communication, it is meant that the passageways merely intersect or join one another. The elongate sheath 28 may be flexible such that the sheath 28 may be advanced to a biopsy site, either through a device, such as a biopsy probe, cannula, etc., or through a biopsy tract created by the biopsy procedure. In any case, variations of the invention may include sheaths 28 that may have sufficient rigidity to access the biopsy cavity (in some cases the sheath 28 may even contain a reinforcing member, e.g., a braid, stiffening member.) The sheath may comprise materials such as polyethylene (PE), especially high density PE (HDPE), nylon, urethane, or a fluoropolymer.

A variation of the inventive device, as illustrated in FIG. 3A, may also contain a delivery device key 38. The delivery device key 38 may be located on the elongated sheath 28 (as illustrated) or may be located on the body 22. As discussed above, it may be necessary to rotate a biopsy probe to retrieve multiple tissue samples. The delivery device key 38 is adapted to be seated into a biopsy probe (not shown) such that when the biopsy probe is rotated, an orientation of the device may match the orientation of the aperture of the biopsy probe. The delivery device key 38 may include a raised protrusion or other surface which may mate with a portion of the biopsy probe. In some variations of the inventive device, the length of the elongate sheath 28 is selected such that when the delivery device key 38 is engaged in a biopsy probe, the distal end of the elongate sheath 28 is located adjacent to an aperture of the biopsy probe.

FIG. 3B illustrates a cross sectional view of a variation of a deployment lock 32 of the inventive device. The deployment lock 32 includes a first end 34 and a second end 36. The first end 34 of the deployment lock 32 is adapted to be inserted into the device body and to engage a portion of a rod (as illustrated below) to at least prevent the rod from distal movement through the device. Thus, "locking" the device. The second end 36 of the deployment lock 32 may be located outside of the device body and is adapted to permit disengagement of the deployment lock 32 from the rod. For example, the variation of the deployment lock 32 depicted in FIG. 3B is adapted to be removed from the device via pulling the second end 36 of the deployment lock 32. While this variation of the deployment lock 32 is designed to be removed from the device, variations of deployment locks of the present invention may remain within the device while simultaneously disengaging from a rod to permit movement of the rod. Additionally, variations of the deployment lock 32 may also contain one or more securing arms 51, which assist in retention of the deployment lock 32 in a "locked" position.

FIG. 3C illustrates a side view of a rod 30 of the present invention. The rod 30 may be a tubular or other member. The rod 30 may have a lumen extending therethrough. The rod 30 may be flexible as required to navigate through a sheath which may itself be located in a biopsy probe. Some materials from which the rod may be constructed include nylon, urethane, PE, and fluoropolymers. As discussed above, the rod 30 may have a portion 42 of increased surface area or increased diameter at a proximal end or along any length of the rod 30. The rod 30 also includes a rod stop 54 located along a length of the rod 30. FIG. 3D illustrates a cross sectional view of the rod stop 54 taken along the line 3D—3D of FIG. 3C. As shown in FIG. 3D, variations of the rod stop 54 may include a rod key 56. The rod key 56 is adapted to mate with the body keyway to maintain the orientation of the rod with respect to the device. Although the rod key 56 depicted in FIG. 3D is a male key, the rod key 56 is intended to mate with the corresponding keyway. Accordingly, the rod key 56 may be a female rather than male fitting. Furthermore, the rod key 56 of the present invention is not limited to placement on the rod stop 54. For example, variations of the inventive device may include a rod key which may be located on a rod 30 as opposed to the rod stop 54.

FIG. 3E illustrates a side view of a variation of an access tube 58 of the present invention. The access tube 58 comprises proximal 68 and distal ends 70 with a lumen 72 extending at least from a portion of the tube 58 through the proximal end 68. In some variations of the invention, the lumen may extend throughout the tube. However, the lumen may also be closed at a distal end 70 such that when a biopsy marker (not shown) is placed in a marker seat 62, the biopsy marker is prevented from advancing distally within the access tube. This is especially useful when side ejection of a marker is desired. In such a case, the closed distal end 70 prevents a marker from remaining within a portion of the lumen 72 of the tube 58 at the distal end 70. The distal end 70 may be either closed or have a occluding member placed therein. The access tube 58 may be flexible as required by the procedure being used to access a biopsy cavity. The access tube 58 may be constructed from materials such as nylon, urethane, PE, or a fluoropolymer.

As illustrated in FIG. 3E, the access tube may also include an access tube stop 60. In this variation, the access tube stop 60 is located at the proximal end 68 of the access tube 58. However, the invention is not limited as such as the access tube stop 60 may be located over any portion of the access tube 58. FIG. 3F illustrates a cross-sectional view of the access tube stop 60 of FIG. 3E as taken along lines 3F—3F. In this variation the access tube stop 60 also contains an access tube key 66. As discussed above, the access tube key 66 mates with a body keyway such that the access tube 58 and marker seat 62 are able to maintain a desired orientation within the device. The access tube key 66 may be male or female depending upon the body keyway.

The access tube 58 will contain a marker seat 62 located towards a distal end 70 of the tube 58. The marker seat 62 will be adapted depending upon the biopsy marker used with the device. For example, a marker seat 62 may be formed by removing a portion of the access tube 58. In some variations of the invention, the invention may have an intermediate member that separates the biopsy marker from the actuating member of the device (e.g., the rod, etc.) and ejects/deploys the marker from the device. The intermediate covering may be discrete from the tube and tissue marker, e.g., a flexible covering 64 as described below. However, it is also contemplated that a portion of the tube itself could be configured to serve as the intermediate member (e.g., a weakened section of a tube that is adapted to fold into the tube lumen to seat the marker and unfold from the lumen to deploy the marker.)

As described above, a variation of the invention includes an intermediate member that is a flexible covering 64. The flexible covering 64 may be located over a portion of the tube 58 which includes the marker seat 62. FIG. 3G illustrates a cross-sectional view of the marker seat 62 taken along the line 3G—3G of FIG. 3E. FIG. 3G illustrates the marker seat 62 covered by the flexible covering 64. As shown, at least a portion of the flexible covering 64 is placed or folded into the marker seat 62. In such variations, the flexible covering 64 assists in deployment of the marker as the flexible covering 64 may be displaced and/or unfolded out of the marker seat 62. In any case, when a flexible covering is used, there may be no contact between any actuator (e.g., rod, etc.) and marker. The flexible covering may be made from any commercially available medical grade flexible material such as polyethylene terephthalate (PET), polytetrafluoroethylene (PTFE), or FEP.

FIG. 3E also illustrates a rod 30 slidably located within the access tube 58 where a distal end of the rod 30 may be located adjacent to the marker seat 62. Distal advancement of the rod 30 advances the access tube 58 within the device. In one variation, the distal end of the rod 30 may be urged against a marker (not shown) seated in the marker seat 62. Since the marker will be constrained within the marker seat, which is located within an elongate sheath (not shown), the marker will be unable to deploy from the marker seat 62. Accordingly, as a result of the rod 30 pushing against the marker (constrained within the marker seat 62) the access tube 58 and marker seat 62 advance with the rod 30. Once the marker is no longer constrained by a sheath, e.g., the marker and marker seat are either placed within or advanced out of an aperture of the biopsy probe, then the force of the rod 30 applied against the marker will eject the marker from the marker seat 62.

In another variation, the distal end of the rod 30 and the lumen 72 of the access tube 58 may be sized such to provide a friction fit between the lumen 72 and the rod 30. Thus, the friction fit permits the rod 30 to advance the access tube 58 until the access tube 58 meets with sufficient resistance to permit the rod 30 to advance independently of the access tube 58. In any case, advancement of the rod 30 in a distal direction advances the marker seat 62 distally until the marker seat 62 is adjacent to the probe aperture such that a marker located in the marker seat 62 may be ejected from the probe aperture.

The invention includes variations where the rod advances the marker seat through a combination of configurations either described herein or known to those familiar with similar delivery devices.

FIG. 3H illustrates a side view of a portion of the access tube 58 of FIG. 3E. In this illustration, the rod 30 is able to advance independently of the access tube 58 and advances into the marker seat 62. As a result, the rod 30 displaces and/or unfolds the flexible covering 64 out of the marker seat 62. Although not illustrated, this action permits the deployment of the marker (not shown) seated within the marker seat 62. In those variations of the invention not having a flexible covering 64, the rod 30 may deploy the marker via direct contact. In such cases, the distal end of the rod 30 is adapted to assist in deploying the marker (e.g., the distal end of the rod may be tapered, rounded, hinged to eject the marker, etc.) Variations of the invention also include a marker seat that permits deployment of a marker through a distal opening in the lumen of the elongate sheath.

FIG. 3I illustrates another variation of the present invention. In this variation, a rod 30 is slidably located within the access tube 58 where a distal end 76 of the rod 30 is adjacent to a fluid 74. In this variation, distal advancement of the rod 30 also advances the access tube 58 within the device when a marker (not shown) is constrained in the marker seat 62 by an outer sheath (not shown.) Such a result occurs as advancement of the rod 30 displaces the fluid 74. Because the marker is constrained in the marker seat 62, the fluid 74 cannot displace the flexible covering 64 from the marker seat 62. Instead, the force on the fluid 74 applied by the distal end 76 of the rod 30 acts to distally advance the marker seat 62 and marker out of the sheath. Once the marker is advanced out of the sheath and is no longer constrained, the force applied by the distal end 76 of the rod 30 displaces the fluid 74 which displaces the flexible covering 64 thereby ejecting the marker from the marker seat 62.

FIG. 3J illustrates a state of the device after the marker is freed from constraint by the sheath. As illustrated, the displacement of the fluid 74 by the distal end of the rod 76 displaces the flexible covering 64 from the marker seat 62 to eject the marker. As illustrated in FIGS. 3I and 3J, the distal end 76 of the rod 30 may be adapted such that it forms a seal (e.g., through sizing, use of a sealing gasket, etc.) with the lumen 72 of the access tube 58.

In some variations of the invention the rod 30 may be entirely replaced with fluid. In such a case, a syringe or similar apparatus would provide an actuator/pressure source to displace the fluid and deploy the marker. Moreover, the flexible covering 64 may also be fluid-tight such that the fluid cannot escape from the device. For example, FIGS. 3I and 3J show the flexible covering 64 as having fluid tight seals 78. It is noted that the position of the seals 78, as illustrated, is merely for exemplary purposes as the seals may be placed in any position such that fluid does not escape. As is apparent, in most cases, the distal end 70 of the access tube 58 will be sealed to prevent leakage of the fluid 74. In some cases, the distal end 70 may be adapted to deliver or leak the fluid in a controlled manner. The fluid 74 may be any biocompatible liquid or gas, e.g., saline fluid, air, etc. In some cases, as the rod 30 exerts a force on the fluid 74, the fluid may compress. In such cases, it may become necessary to add additional fluid 74 to the device.

FIG. 3K illustrates a variation of an access tube 58 for use with the present invention. As illustrated, the distal end 70 of the access tube 58 may be tapered to permit the access tube 58 to enter a cavity where tissue has collapsed or narrowed the tract entering the cavity.

It should be noted that the rod 30 and access tube 58 of the present invention may be sufficiently flexible to navigate through a biopsy probe, cannula, etc., to access a biopsy site. However, some applications may require variations of the invention having a rigid access tube and rod.

FIG. 4A illustrates a cross sectional view of a portion of a variation of inventive delivery device 20. As illustrated, the device 20 is in a "locked" position as the deployment lock 32 engages a portion of the rod 30 to prevent at least distal movement of the rod 30. In this variation, a first end 34 of the deployment lock 32 engages a rod stop 54 on a rod 30. Although the deployment lock 32 may be removed from the body 22, variations of the invention contemplate that the deployment lock 32 may disengage from the rod 30 while remaining attached to the body 22. As mentioned above, in variations of the device 20 for use with a biopsy probe (not shown), the device may have a delivery device key (not shown) as well. The delivery device key permits the orientation of the device to match the orientation of the probe aperture as it is rotated within the body of a patient. Moreover, the delivery device key may be placed such that the distal end of the elongate sheath 28 is placed adjacent to the probe aperture when the delivery device key is engaged to the biopsy probe.

FIG. 4B illustrates a cross sectional view of a portion of the variation of the inventive delivery device 20 where the deployment lock (not shown) is removed from the body 22 via an opening 52 in the body 22. As a result, the rod 30 is able to be advanced in a distal direction within the device 20. As described above, advancement of the rod 30 permits advancement of a access tube 58 within the device 20. As illustrated in FIG. 4B, once an access tube stop 60 engages a distal end 24 of the body 22, the access tube 58 is prevented from further distal movement. Therefore, once the access tube 58 advances out of a distal end of the elongated sheath 28, the access tube stop 60 engages the distal end 24 of the body 22 preventing further distal movement. However, the access tube 58 advances sufficiently to permit advancement of the marker seat out of the distal end of the sheath 28. In some variations of the inventive device 20, the body 22 may also contain a keyway (not shown) as discussed above. Accordingly, the access tube 58 will contain a corresponding key which permits the orientation of the access tube to match the orientation of the device. Maintaining this orientation may also permit the marker seat to be oriented within the device 20 such that it is aligned with an aperture of a probe to permit deployment of the marker through the probe aperture.

In variations of the invention not having an access tube stop 60, distal movement of the rod 30 advances the marker seat distally due to the distal end of the rod pushing against a marker within the marker seat. Since the marker is constrained by the sheath and/or biopsy probe, it remains within the marker seat. Once the marker is advanced out of the sheath 28 and is placed adjacent to the probe-aperture, it is no longer constrained by the sheath 28 or the biopsy probe. At this point, further distal movement of the rod 30 ejects the now unconstrained marker from the marker seat through the probe aperture and into a biopsy cavity.

FIG. 4C illustrates a cross sectional view of the device 20 of FIG. 4B where the rod 30 is further distally advanced to deploy a marker. In this variation, the rod contains a rod stop 54 which limits the distal advancement of the rod 30. Accordingly, the device 20 will be configured such that the rod 30 is able to deploy the marker prior to being prevented from further distal advancement.

FIGS. 5A–5B illustrate a partial cross sectional view of a variation of a delivery device of the present invention for use with a biopsy probe 10. FIG. 5A illustrates the inventive delivery device after the access tube 58 is advanced out of the elongate sheath 28. As discussed above, the elongate sheath 28 may be placed immediately adjacent to an aperture 14 of the probe 10 and the access tube 58 is advanced within the aperture 14. Also as discussed above, the device may permit orientation of the components of the device with the aperture 14 of the probe 10.

FIG. 5B illustrates the invention where the rod 30 may move independently of the access tube 58. In variations of the device having a marker 100 seated in the marker seat 62 upon a flexible covering 64, distal movement of the rod 30 may force the flexible covering 64 out of the marker seat 62 thereby deploying the marker 100.

FIG. 5C illustrates the use of the inventive device used with a probe 10 that contains a distal aperture 14 (e.g., a biopsy needle, etc.) In this case, the device is advanced out of the aperture 14 so that the marker 100 may be deployed in a biopsy cavity. FIG. 5D illustrates another variation of the inventive device where a distal end 70 of the rod 30 permits advancement of the device through a tissue tract (the channel leading from the biopsy cavity to the outside of the patient's body which is created during the biopsy procedure) that may constrict in diameter. It is noted that the sheath 28 may also be adapted to facilitate advancement through a narrowed tissue tract. For instance, if a biopsy probe is removed from the site, the device illustrated in FIG. 5D may be solely advanced into the tissue tract to deposit the biopsy marker 100. Furthermore, the device illustrated in FIG. 5D may be used with a biopsy probe as shown in FIG. 5C.

From the foregoing, it is understood that the invention provides an improved biopsy marker delivery system. While the above descriptions have described the invention for use in the marking of biopsy cavities made through a vacuum-assisted breast biopsy procedure, the invention is not limited to such. The invention disclosed herein may be used with any biopsy procedure discussed herein or otherwise known.

The invention herein has been described by examples and a particularly desired way of practicing the invention has been described. However, the invention as claimed herein is not limited to that specific description in any manner. Equivalence to the description as hereinafter claimed is considered to be within the scope of protection of this patent.

We claim as our invention:

1. A tissue marker delivery device comprising:
    a tube having a lumen extending therethrough;
    a tissue marker removably seated in a marker seat at a distal end of said tube;
    a rod slidably located within the tube lumen;
    an intermediate member extending the length of the marker seat and separating said rod from said tissue marker, where advancement of said rod in a distal direction displaces the intermediate member to displace the tissue marker from said marker seat; and
    a deployment lock having a portion removably attached to the tube, wherein when the portion contacts the rod, the rod is prevented from moving.

2. The tissue marker delivery device of claim 1, wherein the intermediate member is discrete from both the rod and the tissue marker.

3. The tissue marker delivery device of claim 1, wherein the intermediate member comprises a flexible covering.

4. The tissue marker delivery device of claim 3, wherein the flexible covering is made from a material selected from the group consisting of polyethylene terephthalate, polytetrafluoroethylene, and FEP.

5. The tissue marker delivery device of claim 1, further comprising a fluid between the rod and the intermediate member, wherein advancement of the rod in a distal direction displaces the fluid to displace the intermediate member.

6. A method for marking a biopsy cavity comprising the steps of:
    providing a delivery device comprising
        a tube having a lumen extending therethrough;
        a rod slideably located in the lumen of the tube;
        a tissue marker removably located at the distal end of the tube; and
        an intermediate member separating the rod from the tissue marker; advancing the delivery device to the biopsy cavity; releasing a deployment lock to permit distal movement of the rod; actuating the rod to displace a portion of the intermediate member of the delivery device; and depositing the tissue marker in the biopsy cavity.

7. The method of claim 6, wherein the delivery device further comprises a fluid between the rod and the intermediate member, where advancement of the rod in a distal direction displaces the fluid to displace the intermediate member.

8. The method of claim 6, wherein the deployment lock comprises a portion removably attached to the tube, wherein when the portion of the deployment lock contacts the rod, the rod is prevented from moving.

9. The method of claim 6, wherein the intermediate member comprises a flexible covering.

10. The method of claim 9, wherein the flexible covering is made from a material selected form the group consisting of polyethylene terephthalate, polytetrafluoroethylene, and FEP.

* * * * *